(12) United States Patent
Chao et al.

(10) Patent No.: US 8,105,827 B2
(45) Date of Patent: Jan. 31, 2012

(54) PROTEIN EXPRESSION SYSTEMS

(75) Inventors: Yu-Chan Chao, Taipei (TW); Catherine Y. Y. Liu, Taipei (TW); Carol P. Y. Wu, I-Lan (TW)

(73) Assignee: Academia Sinica, Taipei (TW)

( * ) Notice: Subject to any disclaimer, the term of this patent is extended or adjusted under 35 U.S.C. 154(b) by 950 days.

(21) Appl. No.: 11/851,042

(22) Filed: Sep. 6, 2007

(65) Prior Publication Data

US 2009/0068703 A1    Mar. 12, 2009

(51) Int. Cl.
*C12N 15/85* (2006.01)
*C12N 15/86* (2006.01)
*C12N 1/21* (2006.01)
*C12N 1/15* (2006.01)
*C12N 5/14* (2006.01)
*C12N 1/19* (2006.01)

(52) U.S. Cl. ............... 435/325; 435/252.3; 435/254.11; 435/254.2; 435/419

(58) Field of Classification Search .................. None
See application file for complete search history.

(56) References Cited

U.S. PATENT DOCUMENTS

| 6,607,882 B1 | 8/2003 | Cox, III et al. |
| 6,814,963 B2 | 11/2004 | Juang et al. |

OTHER PUBLICATIONS

Lu et al. (Trans-Activation of a Cell Housekeeping Gene Promoter by the IE1 Gene Product of Baculovirus, Virology, 218, pp. 103-113, 1996).*
Geist et al. (Immediate Early Gene 2 of Human Cytomegalovirus Increases Interleukin 2 Receptor-_Gene Expression, Journal of Investigative Medicine, vol. 48, No. 1, 2000, pp. 60-65).*
Dai et al., "The Acidic Activation Domains of the Baculovirus Transactivators IE1 and IE0 are Functional for Transcriptional Activation in Both Insect and Mammalian Cells," *Journal of General Virology*, 85:573-582 (2004).
Fujita et al., "Expression of *Autographa californica* Multiple Nucleopolyhedrovirus Genes in Mammalian Cells and Upregulation of the Host β-*Actin* Gene," *Journal of Virology*, 80(5):2390-2395 (2006).
Hofmann et al., "Efficient Gene Transfer into Human Hepatocytes by Baculovirus Vectors," *Proc. Natl. Acad. Sci.*, 92:10099-10103 (1995).
Kanellos et al., "DNA Vaccination Can Protect *Cyprinus carpio* Against Spring Viraemia of Carp Virus," *Vaccine*, 24: 4927-4933 (2006).
Kanellos et al., "The Safety and Longevity of DNA Vaccines for Fish," *Immunology*, 96:307-313 (1999).
Kenoutis et al., "Baculovirus-Mediated Gene Delivery into Mammalian Cells Does Not Alter Their Transcriptional and Differentiating Potential but Is Accompanied by Early Viral Gene Expression," *Journal of Virology*, 80(8):4135-4146 (2006).
Murges et al., "Baculovirus Transactivator IE1 is Functional in Mammalian Cells," *Journal of General Virology*, 78:1507-1510 (1997).
Olson et al., "The Highly Conserved Basic Domain I of Baculovirus IE1 is Required for *hr* Enhancer DNA Binding and *hr*-Dependent Transactivation," *Journal of Virology*, 77(10):5668-5677 (2003).
Prikhod'ko et al., "In Vivo and In Vitro Analysis of Baculovirus *ie-2* Mutants," *Journal of Virology*, 73(3):2460-2468 (1999).
Rodems, S. and Friesen, P., "The hr5 Transcriptional Enhancer Stimulates Early Expression from the *Autographa californica* Nuclear Polyhedrosis Virus Genome but is Not Required for Virus Replication," *Journal of Virology*, 67(10):5776-5785 (1993).
Rodems, S. and Friesen, P., "Transcriptional Enhancer Activity of *hr5* Requires Dual-Palindrome Half Sites that Mediate Binding of a Dimeric Form of the Baculovirus Transregulator IE1," *Journal of Virology*, 69(9):5368-5375 (1995).
Viswanathan et al., "The Homologous Region Sequence (hr1) of *Autographa californica* Multinucleocapsid Polyhedrosis Virus Can Enhance Transcription from Non-Baculoviral Promoters in Mammalian Cells," *The Journal of Biological Chemistry*, 278(52):52564-52571 (2003).

* cited by examiner

*Primary Examiner* — Suzanne M Noakes
*Assistant Examiner* — Jae W Lee
(74) *Attorney, Agent, or Firm* — Occhiuti Rohlicek & Tsao LLP

(57) ABSTRACT

Disclosed are recombinant non-insect host cells and use of activation of CMV or SV40 promoters by IE1, IE2 and the enhancer hr of the baculovirus in non-insect host cells for expression heterologous RNAs or polypeptides. Also disclosed are methods of using the cells.

18 Claims, 1 Drawing Sheet

PROTEIN EXPRESSION SYSTEMS

BACKGROUND

A number of protein expression systems have been utilized to produce useful heterologous proteins. *Escherichia coli* is one of the most widely used hosts. While high levels of expression in bacterial systems are common, problems of improper folding and lack of post-translational processing often lead to functionally inactive proteins. The baculovirus expression system can be used to circumvent these problems. The baculovirus system enjoys many advantages for expressing a heterologous protein. For example, heterologous cDNA is expressed well although genes having introns are expressed less efficiently. Baculovirus expression of heterologous genes permits folding, post-translational modification, and oligomerization in manners often identical to those in vertebrate cells, e.g., mammalian cells. Further, proteins may be secreted from cells or targeted to different subcellular locations. Single polypeptide, dimeric and trimeric proteins have also been expressed in baculovirus systems. In addition, high level protein expression can be achieved using the strong polyhedrin promoter. Despite these advantages, baculovirus systems are still not satisfactory compared with vertebrate cell-based systems in several aspects. Examples include inefficient secretion from cells, improperly protein folding, and intracellular protein aggregation. Also, N-linked glycosylation sites are often either fully glycosylated or not glycosylated at all, as opposed to various glycoforms in mammalian cells. Further, species- or tissue-specific modifications are unlikely to occur in baculovirus expression systems. Mammalian cell-based expression systems generally do not have the problems seen in baculovirus expression systems. However, protein expression levels are often not satisfactory.

SUMMARY

This invention relates to vertebrate cell-based expression systems that take advantage of baculovirus proteins and nucleic acids so as to achieve high level expression in vertebrate cells. Examples of the baculovirus proteins *Autographa californica* nucleopolyhedrovirus (AcMNPV) immediately early (IE) protein IE1 (Kovacs et al. J Virol. December 1992; 66(12):7429-37), and IE2 (Yoo and Guarino Virology 1994; 202: 164-72) examples of the baculovirus nucleic acids include AcMNPV homologous region (hr) (Viswanathan et al. JBC December; 278 (52): 52564-71) enhancers.

Accordingly, this invention features a cultured recombinant vertebrate receptive cell comprising a first nucleic acid containing a CMV or a SV40 promoter sequence that is operably linked to a sequence encoding an RNA; and a second nucleic acid containing a sequence encoding a protein containing the sequence of an IE1 or IE2 polypeptide. The sequence encoding the protein can be operatively linked to a heterologous promoter, e.g., a non-baculoviral promoter. The cell includes protein of IE1 or IE2, and the protein transactivates the transcription of its target genes in the cell. In other words, the cell expresses functional protein of IE1 or IE2. The cell can further include a third nucleic acid containing the sequence of an hr enhancer. Listed below are exemplary sequences of IE1, IE2, CMV promoter, SV40 promoter, and nine hr enhancers.

```
IE1 polypeptide sequence (582 aa; SEQ ID NO: 1):
MTQINFNASYTSASTPSRASFDNSYSEFCDKQPNDYLSYYNHPTPDGADTVISDSETAAASNFLASVNSL

TDNDLVECLLKTTDNLEEAVSSAYYSESLEQPVVEQPSPSSAYHAESFEHSAGVNQPSATGTKRKLDEYL

DNSQGVVGQFNKIKLRPKYKKSTIQSCATLEQTINHNTNICTVASTQEITHYFTNDFAPYLMRFDDNDYN

SNRFSDHMSETGYYMFVVKKSEVKPFEIIFAKYVSNVVYEYTNNYYMVDNRVFVVTFDKIRFMISYNLVK

ETGIEIPHSQDVCNDETAAQNCKKCNFVDVHHTFKAALTSYFNLDMYYAQTTFVTLLQSLGERKCGFLLS

KLYEMYQDKNLFTLPIMLSRKESNEIETASNNFFVSPYVSQILKYSESVQFPDNPPNKYVVDNLNLIVNK

KSTLTYKYSSVANLLFNNYKYHDNIASNNNAENLKKVKKEDGSMHIVEQYLTQNVDNVKGHNFIVLSFKN

EERLTIAKKNKEFYWISGEIKDVDVSQVIQKYNRFKHHMFVIGKVNRRESTTLHNNLLKLLALILQGLVP

LSDAITFAEQKLNCKYKKFEFN

Nucleotide sequence encoding SEQ ID NO: 1 (1749 bp; SEQ ID NO: 2):
ATGACGCAAATTAATTTTAACGCGTCGTACACCAGCGCTTCGACGCCGTCCCGAGCGTCGTTCGACAACA

GCTATTCAGAGTTTTGTGATAAACAACCCAACGACTATTTAAGTTATTATAACCATCCCACCCCGGATGG

AGCCGACACGGTGATATCTGACAGCGAGACTGCGGCAGCTTCAAACTTTTTGGCAAGCGTCAACTCGTTA

ACTGATAATGATTTAGTGGAATGTTTGCTCAAGACCACTGATAATCTCGAAGAAGCAGTTAGTTCTGCTT

ATTATTCGGAATCCCTTGAGCAGCCTGTTGTGGAGCAACCATCGCCCAGTTCTGCTTATCATGCGGAATC

TTTTGAGCATTCTGCTGGTGTGAACCAACCATCGGCAACTGGAACTAAACGGAAGCTGGACGAATACTTG

GACAATTCACAAGGTGTGGTGGGCCAGTTTAACAAAATTAAATTGAGGCCTAAATACAAGAAAAGCACAA

TTCAAAGCTGTGCAACCCTTGAACAGACAATTAATCACAACACGAACATTTGCACGGTCGCTTCAACTCA

AGAAATTACGCATTATTTTACTAATGATTTTGCGCCGTATTTAATGCGTTTCGACGACAACGACTACAAT

TCCAACAGGTTCTCCGACCATATGTCCGAAACTGGTTATTACATGTTTGTGGTTAAAAAAAGTGAAGTGA

AGCCGTTTGAAATTATATTTGCCAAGTACGTGAGCAATGTGGTTTACGAATATACAAACAATTATTACAT
```

-continued

```
GGTAGATAATCGCGTGTTTGTGGTAACTTTTGATAAAATTAGGTTTATGATTTCGTACAATTTGGTTAAA

GAAACCGGCATAGAAATTCCTCATTCTCAAGATGTGTGCAACGACGAGACGGCTGCACAAAATTGTAAAA

AATGCCATTTCGTCGATGTGCACCACACGTTTAAAGCTGCTCTGACTTCATATTTTAATTTAGATATGTA

TTACGCGCAAACCACATTTGTGACTTTGTTACAATCGTTGGGCGAAAGAAAATGTGGGTTTCTTTTGAGC

AAGTTGTACGAAATGTATCAAGATAAAAATTTATTTACTTTGCCTATTATGCTTAGTCGTAAAGAGAGTA

ATGAAATTGAGACTGCATCTAATAATTTCTTTGTATCGCCGTATGTGAGTCAAATATTAAAGTATTCGGA

AAGTGTGCAGTTTCCCGACAATCCCCCAAACAAATATGTGGTGGACAATTTAAATTTAATTGTTAACAAA

AAAAGTACGCTCACGTACAAATACAGCAGCGTCGCTAATCTTTTGTTTAATAATTATAAATATCATGACA

ATATTGCGAGTAATAATAACGCAGAAAATTTAAAAAAGGTTAAGAAGGAGGACGGCAGCATGCACATTGT

CGAACAGTATTTGACTCAGAATGTAGATAATGTAAAGGGTCACAATTTTATAGTATTGTCTTTCAAAAAC

GAGGAGCGATTGACTATAGCTAAGAAAAACAAAGAGTTTTATTGGATTTCTGGCGAAATTAAAGATGTAG

ACGTTAGTCAAGTAATTCAAAAATATAATAGATTTAAGCATCACATGTTTGTAATCGGTAAAGTGAACCG

AAGAGAGAGCACTACATTGCACAATAATTTGTTAAAATTGTTAGCTTTAATATTACAGGGTCTGGTTCCG

TTGTCCGACGCTATAACGTTTGCGGAACAAAAACTAAATTGTAAATATAAAAAATTCGAATTTAATTAA

IE2 polypeptide sequence (408 aa; SEQ ID NO: 3):
MSRQINAATPSSSRRHRLSLSRRRINFTTSPEAQPSSSSRSQPSSSSRSHRRQERRQEQRVSEENVQIIG

NVNEPLTRTYHRQGVTYYVHGQVNISNDDPLLSQEDDVILINSENVDRERFPDITAQQYQDNIASETAAQ

RALQRGLDLEAQLMNEIAPRSPTYSPSYSPNYVIPQSPDLFASPQSPQPQQQQQQQSEPEEEVEVSCNIC

FTTFKDTKNVNSSFVTSIHCNHAVCFKCYVKIIMDNSVYKCFCSATSSDCRVYNKHGYVEFMPINVTRNQ

DSIKQHWRELLENNTVNNHTTDLNYVEQLQKELSELRAKTSQVEHKMTMLNSDYIMLKHKHAVAELDLQK

ANYDLQESTKKSEELQSTVNNLQEQLRKQVAESQAKFSEFERSNSDLVSKLQTVMSRR

Nucleotide sequence encoding SEQ ID NO: 3 (1227 bp; SEQ ID NO: 4):
ATGAGTCGCCAAATCAACGCCGCCACTCCCAGCAGCAGCCGCCGCCACAGGCTGTCTCTCAGCCGTCGCC

GCATCAACTTTACAACATCTCCCGAAGCCCAGCCGTCTTCAAGCAGTCGCAGCCAGCCGTCTTCAAGCAG

TCGCAGCCATCGCCGTCAGGAGCGGCGTCAGGAGCAGCGTGTCAGCGAAGAAAACGTGCAGATTATCGGG

AACGTCAACGAGCCGTTGACGCGCACCTACCATCGTCAGGGTGTCACGTATTACGTGCACGGTCAGGTTA

ACATTAGCAATGACGATCCGCTATTAAGTCAAGAGGATGACGTCATACTAATTAATAGTGAAAATGTGGA

TCGTGAACGGTTTCCCGACATCACTGCCCAGCAGTACCAGGATAACATTGCGTCGGAGACAGCTGCGCAG

AGGGCTCTGCAACGAGGTTTAGATCTTGAGGCTCAGCTGATGAATGAGATTGCCCCAAGGTCTCCCACTT

ATAGTCCATCTTATTCGCCGAATTACGTAATACCACAGTCGCCAGATTTGTTTGCCTCGCCGCAGTCTCC

GCAGCCGCAGCAGCAGCAGCAGCAGCAATCAGAACCCGAAGAAGAAGTAGAGGTTTCGTGTAATATTTGT

TTTACTACTTTTAAAGACACTAAAAACGTAAATTCCTCGTTTGTGACTTCGATTCATTGTAACCATGCTG

TGTGTTTCAAGTGTTATGTCAAGATAATTATGGACAATTCTGTGTACAAATGTTTTTGCAGCGCTACTTC

ATCAGATTGTCGCGTGTACAATAAGCACGGGTATGTAGAATTTATGCCCATTAACGTCACTCGTAACCAG

GATTCCATCAAACAGCATTGGCGCGAGCTTTTAGAAAATAACACGGTCAACAATCACACCACGGACTTGA

ACTATGTGGAGCAATTGCAAAAAGAACTGTCCGAGCTGCGAGCCAAGACCAGCCAAGTTGAACATAAAAT

GACCATGTTAAACAGCGACTACATTATGCTTAAACACAAGCATGCTGTCGCCGAATTAGATTTACAAAAG

GCAAACTATGACTTGCAAGAATCTACCAAGAAATCAGAAGAGTTGCAATCGACTGTGAATAATCTGCAAG

AACAATTGCGTAAGCAGGTGGCCGAGTCTCAAGCCAAATTTTCAGAGTTTGAGCGCAGTAACTCTGATTT

AGTTTCTAAGTTACAAACTGTTATGTCTAGACGTTAA

CMVie promoter sequence (577 bp; SEQ ID NO: 5):
ATTAATAGTAATCAATTACGGGGTCATTAGTTCATAGCCCATATATGGAGTTCCGCGTTACATAACTTAC
```

-continued

GGTAAATGGCCCGCCTGGCTGACCGCCCAACGACCCCCGCCCATTGACGTCAATAATGACGTATGTTCCC

ATAGTAACGCCAATAGGGACTTTCCATTGACGTCAATGGGTGGAGTATTTACGGTAAACTGCCCACTTGG

CAGTACATCAAGTGTATCATATGCCAAGTCCGCCCCCTATTGACGTCAATGACGGTAAATGGCCCGCCTG

GCATTATGCCCAGTACATGACCTTACGGGACTTTCCTACTTGGCAGTACATCTACGTATTAGTCATCGCT

ATTACCATGCTGATGCGGTTTTGGCAGTACACCAATGGGCGTGGATAGCGGTTTGACTCACGGGGATTTC

CAAGTCTCCACCCCATTGACGTCAATGGGAGTTTGTTTTGGCACCAAAATCAACGGGACTTTCCAAAATG

TCGTAATAACCCCGCCCCGTTGACGCAAATGGGCGGTAGGCGTGTACGGTGGGAGGTCTATATAAGCAGA

CGTCGTTTAGTGAACCG

CMVm promoter sequence (150 bp; SEQ ID NO: 6):
AGGCGTGTACGGTGGGAGGCCTATATAAGCAGAGCTCGTTTAGTGAACCGTCAGATCGCCTGGAGACGCC

ATCCACGCTGTTTTGACCTCCATAGAAGACACCGGGACCGATCCAGCCTCCGCGGCCCCGAATTCGAGCT

CGCAGCTGGC

SV40 promoter sequence (326 bp; SEQ ID NO: 7):
CCAGGCAGGCAGAAGTATGCAAAGCATGCATCTCAATTAGTCAGCAACCAGGTGTGGAAAGTCCCCAGGC

TCCCCAGCAGGCAGAAGTATGCAAAGCATGCATCTCAATTAGTCAGCAACCATAGTCCCGCCCCTAACTC

CGCCCATCCCGCCCCTAACTCCGCCCAGTTCCGCCCATTCTCCGCCCCATGGCTGACTAATTTTTTTTAT

TTATGCAGAGGCCGAGGCCGCCTCTGCCTCTGAGCTATTCCAGAAGTAGTGAGGAGGCTTTTTTGGAGGC

CTAGGCTTTTGCAAAAAGCTCCCGGGAGCTTGTATATCCATTTTCG

AcMNPV hr1 sequence (553 bp; SEQ ID NO: 8)
CATACTCGAGACTAGTAAATGACATTATCCCTCGATTGTGTTTTACAAGTAGAATTCTACCCGTAAAGCG

AGTTTAGTTTTGAAAAACAAATGACATCATTTGTATAATGACATCATCCCCTGATTGTGTTTTACAAGTA

GAATTCTATCCGTAAAGCGAGTTCAGTTTTGAAAACAAATGAGTCATACCTAAACACGTTAATAATCTTC

TGATATCAGCTTATGACTCAAGTTATGAGCCGTGTGCAAAACATGAGATAAGTTTATGACATCATCCACT

GATCGTGCGTTACAAGTAGAATTCTACTCGTAAAGCCAGTTCGGTTATGAGCCGTGTGCAAAACATGACA

TCAGCTTATGACTCATACTTGATTGTGTTTTACGCGTAGAATTCTACTCGTAAAGCGAGTTCGGTTATGA

GCCGTGTGCAAAACATGACATCAGCTTATGAGTCATAATTAATCGTGCGTTACAAGTAGAATTCTACTCG

TAAAGCGAGTTGAAGGATCATATTTAGTTGCGTTTATGAGATAAGATGTAGTGCTCGAGTAAA

AcMNPV hr1a DNA sequence (118 bp; SEQ ID NO: 9)
GTTTTACGAGTAGAATTCTACGTGTAACACACGATCTAAAAGATGATGTCATTTTTTATCAATGACTCAT

TTGTTTTAAAACAGACTTGTTTTACGAGTAGAATTCTACGTGTAAAGC

AcMNPV hr2 sequence (669 bp; SEQ ID NO: 10):
GCTTTACGAGTAGAATTCTACGTGTAAAACATAATCAAGAGATGATGTCATTTGTTTTTCAAAACTGAAC

TCAAGAAATGATGTCATTTGTTTTTCAAAACTGAACTGGCTTTACGAGTAGAATTCTACTTGTAACGCAT

GATCAAGGGATGATGTCATTTGTTTTTCAAAACCGAACTCGCTTTACGAGTAGAATTCTACTTGTAAAAC

ATAATCGAAAGATGATGTCATTTGTTTTTTAAAATTGAACTGGCTTTACGAGTAGAATTCTACTTGTAAA

ACACAATCGAGAGATGATGTCATATTTTGCACACGGCTCTAATTAAACTCGCTTTACGAGTAAAATTCTA

CTTGTAACGCATGATCAAGGGATGATGTATTGGATGAGTCATTTGTTTTTCAAAACTAAACTCGCTTTAC

GAGTAGAATTCTACTTGTAACGCACGCCCAAGGGATGATGTCATTTATTTGTGCAAAGCTGATGTCATCT

TTTGCACACGATTATAAACACAATCAAATAATGACTCATTTGTTTTTCAAAACTGAACTCGCTTTACGAG

TAGAATTCTACTTGTAAAACACAATCAAGCGATGATGTCATTTAAAAATGATGTCATTTGTTTTTCAAA

ACTAAACTCGCTTTACGAGTAGAATTCTACGTGTAAAAC

AcMNPV hr2a sequence (30 bp; SEQ ID NO: 11)
TTTTTACAAATGGAAATGTATTTGTAAAAC

-continued

```
AcMNPV hr3 sequence (666 bp; SEQ ID NO: 12)
GATTTACGCGTAGAATTCTACTTGTAAAGCAAGTTAAAATAAGCCGTGTGCAAAAATGACATCAGACAAA

TGACATCATCTACCTATCATGATCATGTTAATAATCATGTTTTAAAATGACATCAGCTTATGACTAATAA

TTGATCGTGCGTTACAAGTAGAATTCTACTCGTAAAGCGAGTTTAGTTTTGAAAAACAAATGAGTCATCA

TTAAACATGTTAATAATCGTGTATAAAGGATGACATCATCCACTAATCGTGCGTTACAAGTAGAATTCTA

CTCGTAAAGCGAGTTCGGTTTTGAAAAACAAATGACATCATTTCTTGATTGTGTTTTACACGTAGAATTC

TACTCGTAAAGTATGTTCAGTTTAAAAAACAAATGACATCATTTTACAGATGACATCATTTCTTGATTAT

GTTTTACAAGTAGAATTCTACTCGTAAAGCAAGTTTAGTTTTAAAAAACAAATGACATCATCTCTTGATT

ATGTTTTACAAGTAGAATTCTACTCGTAAAGCGAGTTTAGTTTTGAAAAACAAATGACATCATCTCTTGA

TTATGTTTTACAAGTAGAATTCTACTCGTAAAGCGAGTTTAGTTTTCAAAAACAAATGACATCATCCCTT

GATCATGCGTTACAAGTAGAATTCTACTCGTAAAGC

AcMNPV hr4a sequence (150 bp; SEQ ID NO: 13)
GCGTTACAAGTAGAATTCTACTGGTAAAGCAAGTTCGGTTGTGAGCCGTGTGCAAAACATGACATCATAA

CTAATCATGTTTATAATCATGTGCAAAATATGACATCATCCGACGATTGTGTTTTACAAGTAGAATTCTA

CTCGTAAAGC

AcMNPV hr4b sequence (486 bp; SEQ ID NO: 14)
GCTTTACGAGTAGAATTTTACTTGTAAAACACAATCAAGAAATGATGTCATTTTTGTACGTGATTATAAA

CATGTTTAAACATGGTACATTGAACTTAATTTTTGCAAGTTGATAAACATGATTAATGTACGACTCATTT

GTTTGTGCAAGTTGATAAACGTGATTAATATATGACTCATATGTTTGTGCAAAAATGATGTCATCGTACA

AACTCGCTTTACGAGTAGAATTCTACTTGTAACGCATGATCAAGGGATGATGTCATTTGTTTTTTTAAAA

TTCAACTCGCTTTACGAGTAGAATTCTACTTGTAAAACACAATCGAGGGATGATGTCATTTGTAGAATGA

TGTCATTTGTTTTTCAAAACCGAACTCGCTTTACGAGTAGAATTCTACTTGTAACGCAAGATCGGTGGAT

GATGTCATTTTAAAAATGATGTCATCGTACAAACTCGCTTTACGAGTAGAATTCTACGTGTAAAAC

AcMNPV hr4c sequence (30 bp; SEQ ID NO: 15)
GTTTTACGCGTAAAATTCTACTGGTAAAAC

AcMNPV hr5 sequence (509 bp; SEQ ID NO: 16)
GCTTTACGAGTAGAATTCTACGCGTAAAACACAATCAAGTATGAGTCATAATCTGATGTCATGTTTTGTA

CACGGCTCATAACCGAACTGGCTTTACGAGTAGAATTCTACTTGTAATGCACGATCAGTGGATGATGTCA

TTTGTTTTTCAAATCGAGATGATGTCATGTTTTGCACACGGCTCATAAACTCGCTTTACGAGTAGAATTC

TACGTGTAACGCACGATCGATTGATGAGTCATTTGTTTTGCAATATGATATCATACAATATGACTCATTT

GTTTTTCAAAACCGAACTTGATTTACGGGTAGAATTCTACTTGTAAAGCACAATCAAAAAGATGATGTCA

TTTGTTTTTCAAAACTGAACTCGCTTTACGAGTAGAATTCTACGTGTAAAACACAATCAAGAAATGATGT

CATTTGTTATAAAAATAAAAGCTGATGTCATGTTTTGCACATGGCTCATAACTAAACTCGCTTTACGGGT

AGAATTCTACGCGTAAAAC
```

The hr enhancer in the third nucleic acid can contain a sequence of one of SEQ ID NOs: 8-16 or a functional equivalent thereof. This third nucleic acid can be either in trans or in cis with the first or second nucleic acid. For example, the first nucleic acid and the hr enhancer can be on the same molecule or on different molecules. In one embodiment, the hr enhancer is in cis with the first or second nucleic acid. The above-described cell can express the protein of IE1 or IE2, which activates the CMV or SV40 promoter, i.e., activates or increases the transcription of a sequence under the control of the promoter.

The terms host cell and recombinant host cell are used interchangeably. Such terms refer not only to the particular subject cell but also to the progeny or potential progeny of such a cell. Because certain modifications may occur in succeeding generations due to either mutation or environmental influences, such progeny may not be identical to the parent cell, but are still included within the scope of the term as used herein. A receptive host cell (i.e., receptive cell) is any suitable vertebrate animal cell, such a non-mammalian vertebrate cell (e.g., a fish cell) or a mammalian cell (e.g., a Chinese hamster ovary (CHO) cell, a HeLa cell, a NIH3T3 cell, a Vero E6 cell, a BHK cell, a 293 cell, a U2-OS cell, or a COS cell). Other suitable receptive cells are known to those skilled in the art. The term "recombinant" when used with reference, e.g., to a cell, or nucleic acid, polypeptide, or vector, indicates that the cell, nucleic acid, polypeptide or vector, has been modified by the introduction of a heterologous nucleic acid or polypeptide or the alteration of a native nucleic acid or polypeptide, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The term heterologous nucleic acid or polypeptide indicates that the nucleic acid or polypeptide comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous polypeptide indicates that the polypeptide comprises two or more subsequences that are not found in the same relationship to each other in nature (e.g., a fusion protein, where the two subsequences are encoded by a single nucleic acid sequence). In one example, the heterologous sequence is a non-baculovirus sequence.

A "nucleic acid" refers to a DNA molecule (e.g., a cDNA or genomic DNA), an RNA molecule (e.g., an mRNA), or a DNA or RNA analog. A DNA or RNA analog can be
   synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The above-mentioned RNA can be either a noncoding RNA or a coding RNAs (i.e., mRNAs, which encodes a polypeptide). Noncoding RNAs are single- or double-stranded RNAs that do not encode polypeptides. Noncoding RNAs affect processes including, but not limited to, transcription, gene silencing, replication, RNA processing, RNA modification, RNA stability, mRNA translation, protein stability, and/or protein translation. Noncoding RNAs include, but are not limited to, small RNAs ("sRNA"), microRNAs ("miRNAs"), small temporal RNAs ("stRNAs"), and/or interspersed element RNAs (IRE RNAs).

"Promoter" refers to a nucleotide sequence, usually upstream (5') to its coding sequence, that controls the expression of the coding sequence by providing the recognition for RNA polymerase and other factors required for proper transcription. Examples of promoter include a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters or enhancers described herein include CMV promoters (e.g., CMVie and CMVm), SV40 promoters, and hr enhancers, as well as their functional equivalents.

The terms "cis-acting sequence" and "cis-acting element" refer to DNA or RNA sequences whose functions require them to be on the same molecule. The terms "trans-acting sequence" and "trans-acting element" refer to DNA or RNA sequences whose function does not require them to be on the same molecule.

The cell or nucleic acid described above can be used to express a useful polypeptide. For this purpose, one can operatively link a nucleic acid encoding the polypeptide to suitable regulatory sequences to generate an expression vector. "Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

One can use the just-described cell to express an RNA or a polypeptide in a cell by culturing the cell in a medium and expressing the RNA or polypeptide in the cell. One can further purify the polypeptide from the cell or the medium by methods known in the art. The phase "culture" or "grow a cell" refers to maintain the cell under a condition suitable for the cell to survive or proliferate.

The invention also features a method of increasing the expression level of a RNA in a receptive cell. The method includes obtaining a receptive cell that includes a first nucleic acid containing a CMV or SV40 promoter sequence that is operably linked a sequence encoding an RNA; and introducing into the cell a second nucleic acid containing a sequence encoding a protein having the sequence of IE1 or IE2. Alternatively, one can obtain a receptive cell that includes the second nucleic acid and then introduce into the cell the first nucleic acid. The method described above can further include introducing into the cell a third nucleic acid containing the sequence of an hr enhancer, such as a sequence of one of SEQ ID NOs: 8-16 or a functional equivalent thereof. "Expression" refers to the transcription and/or translation of an endogenous gene or a transgene in cells. For example, in the case of antisense constructs, expression may refer to the transcription of the antisense nucleic acid only. In addition, expression refers to the transcription and stable accumulation of sense (mRNA) or functional RNA. Expression may also refer to the production of protein. The cell can be a non-insect cell, e.g., a vertebrate cell (such as a mammalian cell and non-mammalian vertebrate cell), in which the CMV or SV40 promoter functions as a promoter. Examples of a non-mammalian vertebrate cell include a fish cell. See, e.g., Kanellos et al., Vaccine April 2006; 24:4927-4933, and Sylvester et al., Immunology, October 1999; 96:307-313).

The details of one or more embodiments of the invention are set forth in the accompanying description below. Other advantages, features, and objects of the invention will be apparent from the detailed description and the claims.

DETAILED DESCRIPTION

Figure 1:
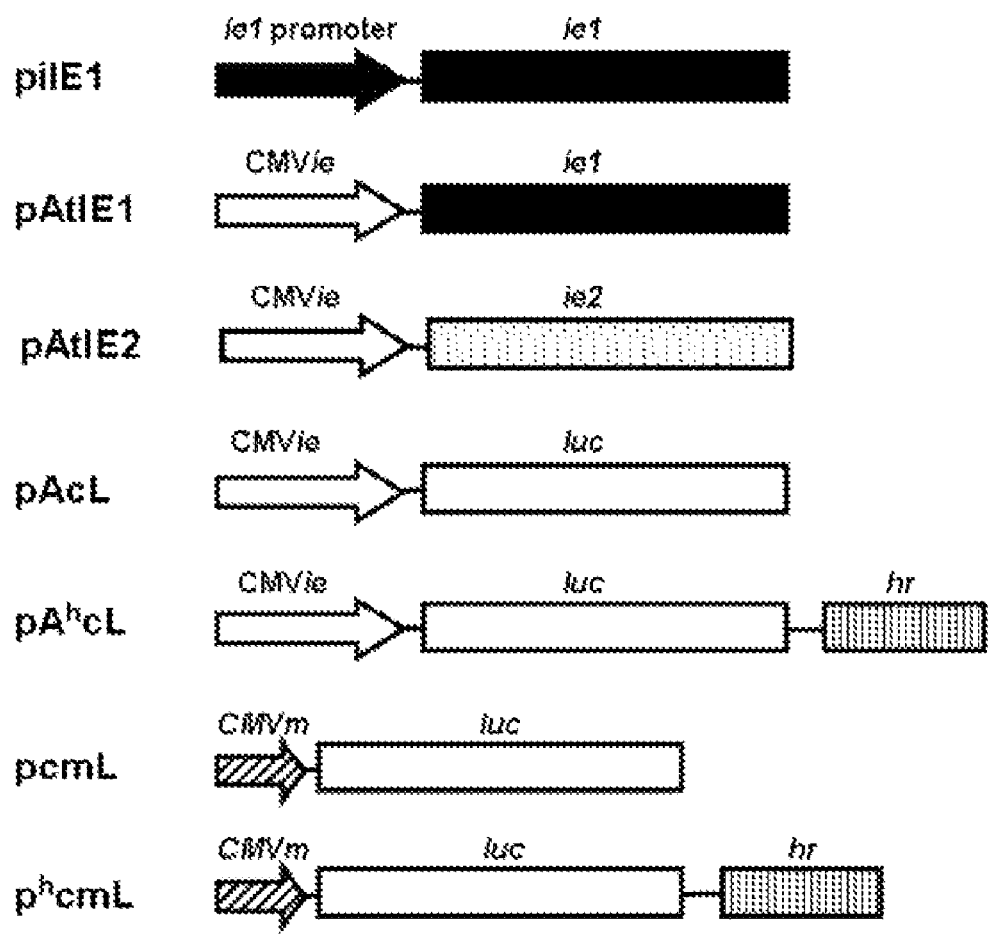
FIG. 1 is a diagram showing construction of exemplary IE1 and IE2-expression vectors and four luciferase (luc) reporter plasmids.

This invention is based, at least in part, on the unexpected discovery that certain baculovirus proteins and nucleic acids increase the expression levels of useful heterologous proteins in expression systems based on non-insect cell animal cells (non-permissive cells).

One aspect of the invention provides a cultured receptive cell which includes a first nucleic acid containing a CMV or a SV40 promoter sequence that is operably linked to a sequence encoding an RNA; and a second nucleic acid containing a sequence encoding a protein containing the sequence of IE1 or IE2. The RNA-encoding nucleic acid is operably linked to the CMV promoter or SV40 promoter. The cell can further include a third nucleic acid containing the sequence of an hr enhancer. In one example, the first nucleic acid and the second nucleic acid are not on the same molecule. That is, none of the first and second nucleic acids are on the same molecule. In other words, the first nucleic acid and the second nucleic acid are in trans, but not in cis. The third nucleic acid can be either in trans or in cis with the first or second nucleic acid. In one example, at least one of the first nucleic acid and the second nucleic acid is heterologous to a baculovirus. For example, the second nucleic acid includes a sequence encoding a protein having the sequence of baculovirus IE1 or IE2 polypeptide, wherein the sequence is under the control of a non-baculoviral promoter. As used herein, an IE1 polypeptide (i.e., IE1) or an IE2 polypeptide (i.e., IE2), refers to any polypeptide having sequences of SEQ ID NO: 1 or 3 (i.e., SEQ ID NO: 1 or 3, or a functional equivalent of SEQ ID NO: 1 or 3). A functional equivalent of a protein sequence, e.g., the IE1 or IE2 protein, refers to a polypeptide derived from the protein sequence, e.g., a fusion polypeptide or a polypeptide having one or more point mutations, insertions, deletions, truncations, or combination thereof. This polypeptide is at least 60% (any number between 60% and 100%, inclusive) identical to, e.g., SEQ ID NO: 1 or 3, and retains substantially activity of the protein, i.e., the ability to enhance the activity of a CMV promoter or a SV40 promoter in a receptive cell using the assay described in the examples below. The functional equivalent polypeptide can contain a fragment of IE1 or IE2. Examples of an IE1 or IE2 functional equivalent include mutants retaining domains important for their transaction activity. It is known in the art that IE1 acidic activation domain is needed for its activity while the RING finger motif of IE2 is not essential for virus replication. See Dai et al. J Gen Virol. March 2004; 85(Pt 3):573-82, and Prikhod'ko et al., J Virol. 1999; 73(3): 2460-2468.

The amino acid composition of IE1 or IE2 polypeptide described herein may vary without disrupting the function of the polypeptide. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in the sequence of IE1 or IE2 is preferably replaced with another amino acid residue from the same side chain family. Alternatively, mutations can be introduced randomly along all or part of the sequence, such as by saturation mutagenesis, and the resultant mutants can be screened for the activities of IE1 or IE2.

Similarly, a functional equivalent of a nucleic acid (e.g., a CMV promoter, a SV40 promoter, or an hr enhancer) refers to a nucleic acid having a sequence derived from one of SEQ ID NO: 5-16, e.g., having one or more point mutations, insertions, deletions, truncations, or combination thereof. This nucleic acid is at least 60% (any number between 60% and 100%, inclusive) identical to anyone of SEQ ID NOs: 5-16 and retains substantially activity of the promoter or enhancer activity. The functional equivalent can contain a fragment of one of SEQ ID NO: 5-16.

Each of the above-described nucleic acid can be a vector, i.e., a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. Examples of a "regulatory sequence" include promoters, enhancers, and other expression control elements (e.g., polyadenylation signals). Regulatory sequences also include those that direct constitutive expression of a nucleotide sequence, as well as tissue-specific regulatory and/or inducible sequences. Additional elements may include heterologous spliced intronic signals.

The cell descried herein can be used to produce (i.e., express) an RNA or a protein of interest. Accordingly, the invention further provides methods for producing an RNA or a protein using the cells. In one embodiment, the method includes culturing the cell (into which a recombinant expression vector encoding the RNA or protein has been introduced)

in a suitable medium such that the RNA or protein is produced. In another embodiment, the method further includes isolating the protein from the medium or the cell.

The protein of interest can be any desired protein, such as therapeutic proteins. Examples of such proteins include cytokines, lymphokines, growth factors, mitogenic factors, chemotactic factors, onco-active factors, receptors, antibody or fragment or variant thereof, channel proteins, G-proteins, signal transduction molecules, and other proteins encoded by disease-related genes. See e.g., U.S. Pat. No. 7,189,690. Preferred proteins include EPO, interleukin family proteins (e.g., IL-6 and IL-8), GM-CSF, and interferon. Other types of proteins include antigenic proteins for vaccination purposes. Examples include the SARS virus Spike protein, influenza viruses HA surface glycoprotein, or their immunogenic fragments. These proteins have specific post-translational modification (e.g., glycosylation) which isn't available in prokaryotic cells, for example.

The design of the expression vector depends on such factors as the choice of a cell to be transformed, the level of expression of protein desired, and the like. The expression vector can be introduced into cells to produce the RNA or polypeptide mentioned above. Examples of a cell include *E. coli* cells, yeast cells, insect cells, non-mammalian vertebrate cells (e.g., fish cells), and mammalian cells. Commercially available fusion expression systems such as GST, MBP, and LacZ can be used. Such fusion proteins are used for purification of the protein. Epitope tags can also be added to recombinant proteins to provide convenient methods of isolation, monitoring expression, and monitoring cellular and subcellular localization, e.g., c-myc, FLAG, or HA.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a encoding sequence under the direction of the polyhedrin promoter or other strong baculovirus promoters. Elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transformation/transfection methods are used to produce bacterial, yeast, insect, or mammalian or non-mammalian vertebrate cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). The terms "transformation" and "transfection" refer to a variety of art-recognized techniques for introducing foreign nucleic acid (e.g., DNA) into a cell. Any of the well known procedures for introducing foreign nucleotide sequences into cells may be used. These include the use of calcium phosphate or calcium chloride co-precipitation, DEAE-dextran-mediated transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a cell (see, e.g., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994). It is only necessary that the particular genetic engineering procedure used be capable of successfully introducing at least one gene into the cell capable of expressing the protein of choice.

The above-mentioned RNA can be an anti-sense RNA, or a small interference RNA (e.g., an RNAi agent) that targets a gene of interest and inhibits its expression activity. The term "RNAi" or "RNA interference" refers to a sequence-specific or selective process by which a target molecule (e.g., a target gene, protein or RNA) is down-regulated. Within the scope of this invention is utilization of RNAi featuring degradation of RNA molecules (e.g., within a cell). The RNAi technology is well known in the art.

The expression system described herein can also be used for expressing a protein or an RNA in a target tissue. Conventional viral and non-viral based gene transfer methods can be used to introduce nucleic acids encoding a desired protein or RNA into target tissues. Such methods can be used to administer nucleic acids for in vivo or ex vivo gene therapy. Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. lipofection is described in e.g., U.S. Pat. Nos. 5,049,386, 4,946,787, and 4,897,355) and lipofection reagents are available commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration). Viral vector delivery systems include DNA and RNA viruses, which have either episomal or integrated genomes after delivery to the cell. The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (cr vivo). Conventional viral based systems include baculoviral, retroviral, lentivirus, adenoviral, adeno-associated, and herpes simplex virus vectors, integration in the host genome is possible with the baculovirus, retrovirus, lentivirus, and adeno-associated virus gene transfer methods, often resulting in long term expression of the inserted transgene.

Ex vivo cell transfection for diagnostics, research, or for gene therapy (e.g., via re-infusion of the transfected cells into the host organism) is well known to those of skill in the art. In one example, cells are isolated from the subject organism, transfected with a nucleic acid (gene or cDNA), and re-infused back into the subject (e.g., a patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients). Stem cells, e.g., hematopoietic stem cells, can be used in ex vivo procedures for cell transfection and gene therapy. The advantage to using stem cells is that they can be differentiated into other cell types in vitro, or can be introduced into a mammal (such as the donor of the cells) where they will engraft in the bone marrow. For example, methods for differentiating CD34+ cells in vitro into clinically important immune cell types using cytokines such a GM-CSF, IFN-γ, and TNF-α are known in the art (see Inaba et al., J. Exp. Med. 176:1693-1702 (1992)).

Vectors (e.g., baculovirus, retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

A number of vertebrate cell expression systems use CMV or SV40 promoters. As discussed herein, baculovirus proteins and nucleic acids boost the activity of these promoters. Accordingly, to increase expression levels from these systems, one can introduce the above-described baculoviral proteins and nucleic acids into the mammalian or non-mammalian vertebrate cell expression using the above-described gene-delivery methods. Alternatively and more conveniently, one simply contacts a non-cytotoxic recombinant baculovirus with the cells so as to supply the baculoviral proteins and nucleic acids.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Material and Methods:
Plasmid Construction:

IE1 and IE2 coding sequences were amplified from baculovirus genomic DNA using the following PCR primers: IE1 forward primer: 5'-CATGGCCATGGTGACGCAAATTAA TTTTAACGCGT-3' (SEQ ID NO: 17) (NcoI site underlined), IE1 reverse primer: 5'-AACCGCTCGAGATTA AATTC GAATTTTTTATA-3' (SEQ ID NO: 18) (XhoI site underlined), IE2 forward primer: 5'-GCCCATGG GTAGTCGCCAAATCAACGCC-3' (SEQ ID NO: 19) (NcoI site underlined) and IE2 reverse primer: 5'-GCCTCGAGAC GTCTAGACATAACAGTTTG-3' (SEQ ID NO: 20) (XhoI site underlined). The resulting PCR fragments were digested with NcoI and XhoI and inserted into pTriex3 vector (Novagen) that was pre-digested also with NcoI and XhoI, generating pAtIE1 and pAtIE2.

The vector pAcL was constructed first by PCR amplifying a luciferase coding sequence with a forward primer: 5'-CCG-GCTCGAGTAGGCGTGTACGGTGG-3' (SEQ ID NO: 21) and a reverse primer: 5% GCCTCTCCC CGGCCGTTGGCCGATTCATTAATGC-3' (SEQ ID NO: 22) (EagI site underlined) using pTRE-luc (Clontech) as a template. The PCR product was digested with PstI and EagI, and the resulting fragment was inserted into pTriex3 pre-digested with PstI and EagI, generating pAcL.

An hr1 fragment was obtained by PCR using AcMNPV genomic DNA as template with a forward primer: 5'-TGA-CATTATCCCTCGATTGTGTTTTACA-3' (SEQ ID NO: 23) and a reverse primer: 5'-TGATCCTTCAACTCGCTTTAC-GAGTAGA-3' (SEQ ID NO: 24). The resulting PCR fragment was cloned into a pCR®-Blunt vector (Invitrogen), generating phr1. The vector phr1 was digested with KpnI and BamHI and the resulting fragment was subsequently cloned into pAcL that was pre-digested with KpnI and BglII, resulting in pA$^h$cL.

The vector piIE1 was constructed by PCR amplifying the IE1 coding sequence plus its promoter region with a forward primer: 5'-TCAACGCCGATCCCTATGAT-3' (SEQ ID NO: 25) and a reverse primer: 5'-AACGTCGCCAACTC-CCATTG-3' (SEQ ID NO: 26). The PCR fragment was cloned into pCR®-Blunt vector (Invitrogen) to yield piIE1.

The constructions of vectors pcmL and p$^h$cmL were described previously in Lo et al., 2002, J. Biol. Chem. 277 (7):5256-64.

Generation of Recombinant Virus:

For ease of single virus selection, a reporter expression cassette with the fluorescent DsR2 gene driven by twin promoters SV40 and CMVm was inserted into all transfer plasmids. The resulting viruses expressed the DsR2 protein in mammalian and insect cells.

Sf21 cells ($2\times10^5$) were seeded in a well of a 24-well plate. Co-transfection experiment was carried out using Cellfectin™ (Invitrogen) as transfection reagent. Each transfection, 1 µg of linear viral DNA (BaculoGold) and 1 µg of transfer plasmids were mixed with 2 µg of Cellfectin™, and the resulting DNA mixture was incubated at room temperature for 25 minutes. The cells were washed with a serum-free TC100 medium and then incubated with the DNA mixture for 5 hours at 26° C. before the DNA mixture was replaced with a 10% FBS TC100 medium. The titer of recombinant virus was determined by either Q-PCR (Lo et al. 2004, Biotechnol. Prog, 20(1):354-60) or $TCID_{50}$.

Cell Culture:

The *Spodoptera frugiperda* IPLB-Sf21 (Sf21) cell line was cultured as monolayer in a TC-100 insect medium containing 10% heat-inactivated fetal bovine serum (FBS). It was used for propagation and infection of wild type and recombinant AcMNPV. CHO-k1 cells were cultured as monolayer in 50% FI2K/50% DMEM (Dulbecco's Minimal Eagle's Medium) containing 10% FBS and 2% antibiotics (Streptomycin and Penicillin) and maintained in 37° C. incubator containing 5% $CO_2$. VeroE6 cells were cultured in MEM (Minimal Eagle's Medium) containing 10% FBS and 2% antibiotics (Streptomycin and Penicillin) and maintained in 37° C. incubator containing 5% $CO_2$.

Transfection:

CHO-k1 cells ($1\times10^4$) or VeroE6 cells ($5\times10^3$) were seeded in each well of a 96-well plate 24 hours prior to transfection. Transfection was performed using lipofectamin2000™ as transfection reagent, following manufacturer's protocol (Invitrogen). In short, solution A was prepared by mixing 0.3 µg of lipofectamin2000 in 20 µl of a serum-free medium. Solution B was prepared by mixing 0.1 µg of total sample DNA in 10 µl of a serum-free medium. Solution A was incubated at room temperature for 5 minutes before mixing with solution B. The resulting mixture was incubated for 25 minutes at room temperature. A serum-free medium (30 µl) was added to the solution mixture to bring up the volume to 60 µl. The cells were washed with a serum-free medium before addition of the solution mixture. The plate was incubated for 4-6 hours at 37° C. with 5% $CO_2$ and the supernatant was replaced with 100 µl of serum- and antibiotics-containing medium. The plate was further incubated at 37° C. in 5% $CO_2$ for additional 2-3 days before luciferase activity assay was carried out.

Mammalian Cell Culture and Virus Transduction Experiments

VeroE6 or CHO-k1 cells cells were seeded on a 96-well plate at $5\times10^3$/well 24 hours prior to experiment. The cells were incubated with recombinant baculovirus at multiplicity of infection (MOI) of 20 (for VeroE6 cells) or MOI of 40 (for CHO-k1 cells). Transduced cells were harvested at 72 hours (VeroE6 cells) or 48 hours (CHO-k1 cells) post-transduction for luciferase activity assay.

Luciferase Assay:

The above-described cells were lysed with 100 µl of a culture cell lysis reagent (CCLR): 100 mM potassium phosphate (pH 7.8), 1 mM EDTA, 10% glycerol, 1% Triton X-100, and 7 mM β-mercaptoethanol. The plate was placed on a rocking platform at 4° C. for 10 minutes at 200 rpm to break the cells. The resulting supernatant was collected into a 1.5 ml micro-centrifuge tube and subjected to centrifugation at 14,000 rpm for 10 minutes at 4° C. Ten microliter of the supernatant and 180 µl of luciferase activity reagent (LAR, 25 mM Tricine (pH 7.8), 15 mM potassium phosphate (pH 7.8), 15 mM $MgSO_4$, 4 mM EGTA, 1 mM ATP, and 0.1 mM dithiothreitol) were mixed on a 96-well assay plate. Fifty microliter of 0.2 mM luciferin (Promega) was injected into each well, and the luciferase activity was measured on a luminometer (Berthold, Lumat LB 9501).

Protein Concentration Determination from Cell Lysate:

The method for protein concentration determination was described previously (Lo et al., 2002, J. Biol. Chem. 277(7): 5256-64). The luciferase activity was expressed as luciferase raw data (RLU)/µg total protein using the following formula: [RLU/(Vol. (µl) of sample used for luciferase assay)]÷[(protein value (ng/µl)×dilution fold)/(1000 µl/ng)]. The relative light unit was obtained by setting the maximum RLU/µg total protein in each figure to around 10. Fold increases were obtained by setting the value of RLU/µg total protein of the reporter plasmid to 1, and comparing all other values to it.

Results:

Baculovirus IE1 Trans-Activated both CMVie and CMVm Promoters in Mammalian Cells Two plasmids constructed to investigate whether baculovirus trans-activator IE1 was capable of trans-activating mammalian CMVie and CMVm promoters. One plasmid, piIE1, contained an IE1 coding sequence that was under its own promoter ie1; the other, pAtIE1IE1, also included the IE1 coding sequence under the CMVie promoter (FIG. 1).

To examine the effects of IE1 on the CMVm promoter, VeroE6 or CHO-k1 cells were transfected with reporter plasmids, pcmL and $p^hcmL$, in the presence or the absence of piIE1 or pAtIE1. Luciferase assays were conducted in the manner described above. It was found that activation of the CMVm promoter was only seen with the $p^hcmL$ plasmid. Specifically, in Vero cells having pcmL, the luciferase activities were not increased in the presence of either piIE1 or pAtIE1. Similar results were found in CHO-k1 cells having pcmL. In contrast, in Vero cells having $p^hcmL$, the luciferase activities, reported vector alone, in the presence of piIE1, and in the presence of pAtIE1, were, respectively, 1.2, 8.2, and 48.5 times of the luciferase activity in Vero cells having pcmL. In CHO-k1 cells having $p^hcmL$, the activities were 4.2, 137, and 110 times of that in CHO-k1 cells having pcmL. These results indicated that the hr sequence was required for IE1-activation of CMVm promoter in both VeroE6 and CHO-k1 cells.

The same experiment was repeated with reporter plasmids pAcL and $pA^hcL$, which included the CMVie promoter. The results were shown in Table 1 below. As shown in the table, about 4-fold increase in luciferase activity was detected when either piIE1 or pAtIE1 was co-transfected with the reporter plasmid pAcL. Together, the results showed that the baculovirus IE1 protein alone could activate the full-length CMVie mammalian promoter in both Vero E6 and CHO-k1 cells.

Baculovirus Homologous Region could Augment IE1-Mediated CMVie and CMVm Promoter Activation both in Cis and in Trans:

Baculovirus hr1 sequence was incorporated into the reporter plasmids pcmL and pAcL to obtain $p^hcmL$ and $pA^hcL$ (FIG. 1). These two reporter plasmids were transfected into VeroE6 and CHO-k1 cells in the presence or the absence of piIE1 or pAtIE1 and the luciferase expressions were compared to those obtained from pcmL and pAcL in the manner described above. Luciferase expression under CMVm promoter was drastically increased (~$10^2$ fold at maximum) when both hr and IE1 were present, mainly because the expression from CMVm without hr was almost negligible. Luciferase expression under CMVie promoter was also greatly increased in the presence of hr (~9-fold at maximum).

To examiner the ability of hr to enhance IE1-mediated activation in trans, a plasmid containing baculovirus hr1 (phrI) was constructed (FIG. 1). It was co-transfected with reporter plasmid pcmL and pAcL with or without piIE1 or pAtIE1 into VeroE6 and CHO-k1 cells. The resulting luciferase expressions were compared to those obtained from $p^hcmL$ and $pA^hcL$ with or without piIE1 or pAtIE1. The results presented in Table 1 below.

TABLE 1

Activation of CMVie promoter IE1 in both Vero E6 and CHO-k1 cells

| Reporter | Plasmids | Relative Light Unit | |
|---|---|---|---|
| | | VeroE6 | CHO-K1 |
| pAcL | reporter only* | 1 x | 1 x |
| | reporter + piIE1 | 4.1 x | 4.4 x |
| | reporter + pAtIE1 | 4.1 x | 4.4 x |
| | reporter + piIE1 + hr1 | 8.5 x | 7.6 x |
| | reporter + pAtIE1 + hr1 | 6 x | 7.3 x |
| $pA^hcL$ | reporter only | 1.3 x | 1.5 x |
| | reporter + piIE1 | 13.5 x | 9 x |
| | reporter + pAtIE1 | 12 x | 6.7 x |

*The luciferase expression level of cells having pAcL reporter only was used as the basal level (1x).

In both types of cells, the presence of a third plasmid having hr in trans almost doubled the luciferase expression under CMVie promoter in the presence of IE1, however, the level of activation did not exceed that for hr in cis. The results indicate that hr augmented IE1-mediated trans-activation of CMV promoter both in trans and in cis in VeroE6 and CHO-k1 cells and that the augmentation was more efficient in cis than in trans.

Similar results were obtained through baculovirus transduction. A number of recombinant baculoviruses were generated to test the efficiency of baculovirus-mediated gene delivery into VeroE6 and CHO-k1 cells, and whether IE1 could mediate mammalian promoter activation when packaged into the baculovirus genome. The recombinant baculoviruses included vAtIE1, which had a CMVie promoter driven IE1-expressing cassette and four reporter viruses: vAcmL, $vA^hcmL$, vAcL, and $vA^hcL$.

VeroE6 cells were transduced with these recombinant viruses at an MOI=10 for each type of virus and CHO-k1 cells were transduced at MOI=20 for each type of virus. Luciferase assays were carried out in the manner described above. The results were summarized in Table 2 below.

TABLE 2

Recombinant baculovirus vAtIE1 activates
CMVm and CMVie promoters

| Promoter | Baculovirus | Relative Light Unit | |
|---|---|---|---|
| | | CHO-K1 | VeroE6 |
| CMVm | vAcmL | 1 x | 1 x |
| | vA$^h$cmL | 1 x | 1 x |
| | vAcmL + vAtIE1 | 2.5 x | 52 x |
| | vA$^h$cmL + vAtIE1 | 4 x | 163 x |
| CMVie | vAcL | 1 x | 1 x |
| | vA$^h$cL | 7.7 x | 12 x |
| | vAcL + vAtIE1 | 2.5 x | 2.5 x |
| | vA$^h$cL + vAtIE1 | 17 x | 38 x |

Note:
The luciferase expression level of vAcmL or vAcL was used as the basal level (1x) for each cell type.

As shown in Table 2, recombinant baculoviruses vAtIE1 activated CMVm and CMVie promoters in both Vero E6 and CHO-k1 cells.

For the CMVm promoter, reporter virus vAcmL or vA$^h$cmL had a very low background level expression in mammalian cells. The addition of IE1 greatly enhanced the CMVm promoter activity in Vero E6 (by 52 folds) while only moderately in CHO-k1 (by 2.5 folds). In both Vero E6 and CHO-k1 cells, the presence of hr did not affect the activity of the CMVm promoter, but augmented the trans-activation effect of IE1. The virus having the expression cassette encoding IE1, vAtIE1, was more effective in Vero E6 cells than in CHO-k1 cells to increase the activity of CMVm, most likely due to the higher transduction efficiency of baculovirus in Vero E6 cells.

For the CMVie promoter, hr increased the CMVie promoter activity by 7.7 and 12 folds in CHO-k1 and Vero E6 cells, respectively. The IE1 virus further increased the activity by 2 to 3 folds (i.e., to 17 and 38 folds of the basal level). The effects of IE1 with regard to the CMVie promote were less significant than those with regard the CMVm promoter.

Overall, the transduction activated the promoters in a fashion similar that in the above-described transient expression, where a combination of IE1 and hr increased the CMVie promoter the most.

IE1 and IE2 Enhanced CMVie Promoter Activity in a Dose-Dependent Manner

Besides IE1, IE2 protein is also a major trans-activator of baculovirus. To examine whether IE2 also activated the mammalian CMVie promoter, an IE2-expressing plasmid, pAtIE2 (FIG. 1), and virus derived from it, vAtIE2, were generated. Three effecter plasmids, piIE1, pAtIE1 and pAtIE2 were separately co-transfected with the reporter pAcL plasmid into Vero E6 cells. For each transfection, the amount of the reporter plasmid was 30 ng, while the effecter plasmid was added at increasing molar ratios (1:1 to 1:5). It was unexpected that IE2 had a much stronger effect on the CMVie promoter activation than IE1. See Table 3 below. It was found that piIE1 increased the CMVie promoter by 12-folds at a ratio of 3:1, while pAtIE2 increased the CMVie promoter 30-folds at the ratio 4:1. When the hr enhancer was present in cis on the reporter plasmid (pA$^h$cL), the IE1- and IE2-mediated activation were even more pronounced, with respective maximum activation rates of 30- and 122-folds at ratio 1:3. The results indicated that that IE2 enhanced the CMVie promoter activity in mammalian cells, and this activation was augmented by the hr sequence in a manner similar to the IE1 activation. The results also indicated that IE2 was a stronger trans-activator for the CMVie promoter than IE1.

TABLE 3

IE1 and IE2 enhanced CMVie promoter
activity in a dose-dependent manner

| IE Expression Vector:Reporter Vector | Relative Light Unit | | |
|---|---|---|---|
| | pAcL + pAtIE1 | pAcL + piIE1 | pAcL + pAtIE2 |
| 0:1 | 1 x | 1 x | 1 x |
| 1:1 | 2 x | 4 x | 20 x |
| 2:1 | 3 x | 6 x | 23 x |
| 3:1 | 3 x | 12 x | 25 x |
| 4:1 | 3 x | 6 x | 31 x |
| 5:1 | 3 x | 8 x | 33 x |
| | pA$^h$cL + pAtIE1 | pA$^h$cL + piIE1 | pA$^h$cL + pAtIE2 |
| 0:1 | 2 x | 2 x | 2 x |
| 1:1 | 5 x | 7 x | 55 x |
| 2:1 | 7 x | 10 x | 108 x |
| 3:1 | 12 x | 30 x | 122 x |
| 4:1 | 12 x | 30 x | 88 x |
| 5:1 | 11 x | 30 x | 89 x |

IE1 and IE2 CMVin Promoter and CMVie Promoter Differentially

Recombinant baculoviruses vAtIE1 and vAtIE2 and wild-type AcMNPV were co-transduced separately with the four reporter viruses, vAcmL, vA$^h$cmL, vAcL and vA$^h$cL. Luciferase assays were conducted in the manner described above. The results were summarized in Table 4 below.

TABLE 4

IE1 and IE2 CMVm promoter and CMVie promoter differentially
Relative Light Unit

| Reporter virus | + none | + wt virus | + vAtIE1 | + vAtIE2 |
|---|---|---|---|---|
| vAcmL | 1 x | 1 x | 1366 x | 39 x |
| vA$^h$cmL | 2 x | 2 x | 1868 x | 142 x |
| vAcL | 54 x | 54 x | 163 x | 996 x |
| vA$^h$cL | 110 x | 110 x | 508 x | 4014 x |

As shown in Table 4, while IE1 was a strong activator of the CMVm promoter in Vero E6, IE2 was a specific strong activator of the CMVie promoter, especially in the presence of the hr sequence in cis with the reporter gene. Using the luciferase expression level of vAcL as the basal control, it was found that IE1-expressing virus could increase the CMVm promoter activity by 1366 folds (without hr) or 1868 folds (with hr). IE1 also increased the CMVie promoter activity by 163 folds and 508 folds in the absence and presence of hr, respectively. IE2 only increased the CMVm promoter by 39 and 142 folds in the absence and presence of hr, respectively, but dramatically up-regulated the CMVie promoter activity by 996 and 4014-folds in the absence and presence of hr enhancement respectively. The wild-type virus, although containing both ie1 and ie2 genes, did not have an effect on the luciferase gene expression. This indicated that both genes requires proper expression (here driven by CMVie promoter) for their function.

In the above study, it was shown for the first time that the two major trans-activators of baculovirus, IE1 and IE2, when properly expressed under a mammalian promoter, could activate a non-baculoviral promoter in mammalian cells. An interesting observation was also made—when driven by its endogenous promoter in naked DNA form (plasmid), IE1 could activate the mammalian CMVie promoter and its derivative. In contrast, wild-type AcMNPV virus itself failed to activate the CMVie promoter even though both ie1 and ie2 genes are present in its genome. This is likely due to ineffective recognition of the IE1 endogenous promoter when packaged within the whole AcMNPV genome.

The mechanism for hr enhancement of the CMVie promoter activity and IE1 or IE2 activation of the promoter are different and additive. Here, it was found that the hr sequence enhanced not only IE1-mediated activation in mammalian cells, but also the IE2-mediated promoter activation.

IE2 activated the mammalian CMVie promoter in Vero E6 cells and was about three times more effective than IE1. However, this activation was only seen on the CMVie promoter, but not the CMVm promoter. There are several possible explanations: 1) IE2 may interact directly with the enhancer part of the CMVie promoter, which is missing in the CMVie promoter; (2) IE2 may act via specific host mechanisms/factors which improve cellular transcription or translation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A cultured recombinant receptive cell comprising
a first nucleic acid containing a CMV or an SV40 promoter sequence that is operably linked to a sequence that is transcribed to an RNA; and
a second nucleic acid containing a sequence encoding the baculovirus immediate early protein 1 (IE1) or the baculovirus immediate early protein 2 (IE2) operably linked to a heterologous promoter sequence,
wherein the cell is a mammalian cell, expresses the IE1 or IE2, and also expresses an increased level of the RNA as compared to that without the second nucleic acid, and wherein the IE1 or IE2 activates the CMV or SV40 promoter.

2. The cell of claim 1, wherein the cell further comprises a third nucleic acid including the sequence of an homologous region (hr) enhancer.

3. The cell of claim 2, wherein the hr enhancer is selected from the group consisting of SEQ ID NO: 8-16.

4. The cell of claim 1, wherein the first nucleic acid further comprises the sequence of an hr enhancer.

5. The cell of claim 4, wherein the hr enhancer is selected from the group consisting of SEQ ID NO: 8-16.

6. The cell of claim 1, wherein the RNA is translated to a polypeptide, thereby expressing an increased level of the polypeptide as compared to that without the second nucleic acid.

7. The cell of claim 1, wherein the first nucleic acid and the second nucleic acid are not on the same molecule.

8. The cell of claim 1, wherein the heterologous promoter sequence is a CMV promoter sequence.

9. A method of producing an RNA in a cell, the method comprising culturing the cell of claim 1 and expressing the RNA in the cell.

10. A method of producing a polypeptide in a cell, the method comprising culturing the cell of claim 6 in a medium, and expressing the polypeptide in the cell.

11. The method of claim 10, wherein the method further comprises purifying the polypeptide from the cell or the medium.

12. A method of increasing the expression level of an RNA in a receptive cell, comprising culturing the cell of claim 1, and expressing the RNA in the cell.

13. The method of claim 12, wherein the method further comprises introducing into the cell a third nucleic acid containing the sequence of an hr enhancer.

14. The method of claim 12, wherein the hr enhancer includes one of SEQ ID NO: 8-16.

15. The method of claim 12, wherein the RNA is translated to a polypeptide.

16. The cell of claim 1, wherein the second nucleic acid contains a sequence encoding the IE2.

17. The cell of claim 1, wherein the cell is produced by transducing a host cell with a recombinant baculovirus containing the second nucleic acid.

18. A method of increasing the expression level of a polypeptide in a receptive cell, comprising culturing the cell of claim 6, and expressing the polypeptide in the cell.

* * * * *

SEQUENCE LISTING

<160> NUMBER OF SEQ ID NOS: 26

<210> SEQ ID NO 1
<211> LENGTH: 582
<212> TYPE: PRT
<213> ORGANISM: Autographa californica nucleopolyhedrovirus

<400> SEQUENCE: 1

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
        195                 200                 205

Tyr Asn Ser Asn Arg Phe Ser Asp His Met Ser Glu Thr Gly Tyr Tyr
    210                 215                 220

Met Phe Val Val Lys Lys Ser Glu Val Lys Pro Phe Glu Ile Ile Phe
225                 230                 235                 240

Ala Lys Tyr Val Ser Asn Val Tyr Glu Tyr Thr Asn Tyr Tyr
            245                 250                 255

Met Val Asp Asn Arg Val Phe Val Thr Phe Asp Lys Ile Arg Phe
            260                 265                 270

Met Ile Ser Tyr Asn Leu Val Lys Glu Thr Gly Ile Glu Ile Pro His
            275                 280                 285

Ser Gln Asp Val Cys Asn Asp Glu Thr Ala Ala Gln Asn Cys Lys Lys
            290                 295                 300

Cys His Phe Val Asp Val His His Thr Phe Lys Ala Ala Leu Thr Ser
305                 310                 315                 320

Tyr Phe Asn Leu Asp Met Tyr Tyr Ala Gln Thr Thr Val Thr Leu
            325                 330                 335

Leu Gln Ser Leu Gly Glu Arg Lys Cys Gly Phe Leu Leu Ser Lys Leu
            340                 345                 350

Tyr Glu Met Tyr Gln Asp Lys Asn Leu Phe Thr Leu Pro Ile Met Leu
            355                 360                 365

Ser Arg Lys Glu Ser Asn Glu Ile Glu Thr Ala Ser Asn Asn Phe Phe
370                 375                 380

Val Ser Pro Tyr Val Ser Gln Ile Leu Lys Tyr Ser Glu Ser Val Gln
385                 390                 395                 400

Phe Pro Asp Asn Pro Pro Asn Lys Tyr Val Val Asp Asn Leu Asn Leu
            405                 410                 415

Ile Val Asn Lys Lys Ser Thr Leu Thr Tyr Lys Tyr Ser Ser Val Ala
            420                 425                 430

Asn Leu Leu Phe Asn Asn Tyr Lys Tyr His Asp Asn Ile Ala Ser Asn
            435                 440                 445

Asn Asn Ala Glu Asn Leu Lys Lys Val Lys Glu Asp Gly Ser Met
450                 455                 460

His Ile Val Glu Gln Tyr Leu Thr Gln Asn Val Asp Asn Val Lys Gly
465                 470                 475                 480

His Asn Phe Ile Val Leu Ser Phe Lys Asn Glu Arg Leu Thr Ile
            485                 490                 495

Ala Lys Lys Asn Lys Glu Phe Tyr Trp Ile Ser Gly Glu Ile Lys Asp
            500                 505                 510

Val Asp Val Ser Gln Val Ile Gln Lys Tyr Asn Arg Phe Lys His His
            515                 520                 525

Met Phe Val Ile Gly Lys Val Asn Arg Arg Glu Ser Thr Thr Leu His
            530                 535                 540

Asn Asn Leu Leu Lys Leu Leu Ala Leu Ile Leu Gln Gly Leu Val Pro
545                 550                 555                 560

Leu Ser Asp Ala Ile Thr Phe Ala Glu Gln Lys Leu Asn Cys Lys Tyr
            565                 570                 575

Lys Lys Phe Glu Phe Asn
            580

<210> SEQ ID NO 2
<211> LENGTH: 1749
<212> TYPE: DNA
<213> ORGANISM: Autographa californica nucleopolyhedrovirus

<400> SEQUENCE: 2
atgacgcaaa ttaattttaa cgcgtcgtac accagcgctt cgacgccgtc ccgagcgtcg      60
ttcgacaaca gctattcaga gttttgtgat aaacaaccca acgactattt aagttattat     120
aaccatccca ccccggatgg agccgacacg gtgatatctg acagcgagac tgcggcagct     180

-continued

```
tcaaacttttt tggcaagcgt caactcgtta actgataatg atttagtgga atgtttgctc      240
aagaccactg ataatctcga agaagcagtt agttctgctt attattcgga atcccttgag      300
cagcctgttg tggagcaacc atcgcccagt tctgcttatc atgcggaatc ttttgagcat      360
tctgctggtg tgaaccaacc atcggcaact ggaactaaac ggaagctgga cgaatacttg      420
gacaattcac aaggtgtggt gggccagttt aacaaaatta aattgaggcc taaatacaag      480
aaaagcacaa ttcaaagctg tgcaacccct gaacagacaa ttaatcacaa cacgaacatt      540
tgcacggtcg cttcaactca agaaattacg cattatttta ctaatgattt tgcgccgtat      600
ttaatgcgtt tcgacgacaa cgactacaat tccaacaggt tctccgacca tatgtccgaa      660
actggttatt acatgtttgt ggttaaaaaa agtgaagtga agccgtttga aattatattt      720
gccaagtacg tgagcaatgt ggtttacgaa tatacaaaca attattacat ggtagataat      780
cgcgtgtttg tggtaacttt tgataaaatt aggtttatga tttcgtacaa tttggttaaa      840
gaaaccggca tagaaattcc tcattctcaa gatgtgtgca acgacgagac ggctgcacaa      900
aattgtaaaa aatgccattt cgtcgatgtg caccacacgt ttaaagctgc tctgacttca      960
tattttaatt tagatatgta ttacgcgcaa accacatttg tgactttgtt acaatcgttg     1020
ggcgaaagaa aatgtgggtt tcttttgagc aagttgtacg aaatgtatca agataaaaat     1080
ttatttactt tgcctattat gcttagtcgt aaagagagta atgaaattga gactgcatct     1140
aataatttct ttgtatcgcc gtatgtgagt caaatattaa agtattcgga aagtgtgcag     1200
tttcccgaca atcccccaaa caaatatgtg gtggacaatt taaatttaat tgttaacaaa     1260
aaaagtacgc tcacgtacaa atacagcagc gtcgctaatc ttttgtttaa taattataaa     1320
tatcatgaca atattgcgag taataataac gcagaaaatt taaaaaaggt taagaaggag     1380
gacggcagca tgcacattgt cgaacagtat ttgactcaga atgtagataa tgtaaagggt     1440 cacaattta tagtattgtc tttcaaaaac gaggagcgat tgactatagc taagaaaaac     1500
aaagagtttt attggatttc tggcgaaatt aaagatgtag acgttagtca agtaattcaa     1560
aaatataata gatttaagca tcacatgttt gtaatcggta aagtgaaccg aagagagagc     1620
actacattgc acaataattt gttaaaattg ttagctttaa tattcaggg tctggttccg     1680 ttgtccgacg ctataacgtt tgcggaacaa aaactaaatt gtaaatataa aaaattcgaa     1740
tttaattaa                                                             1749
```

<210> SEQ ID NO 3
<211> LENGTH: 408
<212> TYPE: PRT
<213> ORGANISM: Autographa californica nucleopolyhedrovirus

<400> SEQUENCE: 3

```
Met Ser Arg Gln Ile Asn Ala Ala Thr Pro Ser Ser Arg Arg His
  1               5                  10                  15

Arg Leu Ser Leu Ser Arg Arg Ile Asn Phe Thr Thr Ser Pro Glu
             20                  25                  30

Ala Gln Pro Ser Ser Ser Ser Arg Ser Gln Pro Ser Ser Ser Arg
         35                  40                  45

Ser His Arg Arg Gln Glu Arg Gln Glu Gln Arg Val Ser Glu Glu
     50                  55                  60

Asn Val Gln Ile Ile Gly Asn Val Asn Glu Pro Leu Thr Arg Thr Tyr
 65                  70                  75                  80

His Arg Gln Gly Val Thr Tyr Tyr Val His Gly Gln Val Asn Ile Ser
                 85                  90                  95
```

```
Asn Asp Asp Pro Leu Leu Ser Gln Glu Asp Val Ile Leu Ile Asn
            100                 105                 110
Ser Glu Asn Val Asp Arg Glu Arg Phe Pro Asp Ile Thr Ala Gln Gln
        115                 120                 125
Tyr Gln Asp Asn Ile Ala Ser Glu Thr Ala Ala Gln Arg Ala Leu Gln
130                 135                 140
Arg Gly Leu Asp Leu Glu Ala Gln Leu Met Asn Glu Ile Ala Pro Arg
145                 150                 155                 160
Ser Pro Thr Tyr Ser Pro Ser Tyr Ser Pro Asn Tyr Val Ile Pro Gln
                165                 170                 175
Ser Pro Asp Leu Phe Ala Ser Pro Gln Ser Pro Gln Pro Gln Gln
            180                 185                 190
Gln Gln Gln Gln Ser Glu Pro Glu Glu Val Glu Val Ser Cys Asn
        195                 200                 205
Ile Cys Phe Thr Thr Phe Lys Asp Thr Lys Asn Val Asn Ser Ser Phe
210                 215                 220
Val Thr Ser Ile His Cys Asn His Ala Val Cys Phe Lys Cys Tyr Val
225                 230                 235                 240
Lys Ile Ile Met Asp Asn Ser Val Tyr Lys Cys Phe Cys Ser Ala Thr
                245                 250                 255
Ser Ser Asp Cys Arg Val Tyr Asn Lys His Gly Tyr Val Glu Phe Met
            260                 265                 270
Pro Ile Asn Val Thr Arg Asn Gln Asp Ser Ile Lys Gln His Trp Arg
        275                 280                 285
Glu Leu Leu Glu Asn Asn Thr Val Asn Asn His Thr Thr Asp Leu Asn
290                 295                 300
Tyr Val Glu Gln Leu Gln Lys Glu Leu Ser Glu Leu Arg Ala Lys Thr
305                 310                 315                 320
Ser Gln Val Glu His Lys Met Thr Met Leu Asn Ser Asp Tyr Ile Met
                325                 330                 335
Leu Lys His Lys His Ala Val Ala Glu Leu Asp Leu Gln Lys Ala Asn
            340                 345                 350
Tyr Asp Leu Gln Glu Ser Thr Lys Lys Ser Glu Leu Gln Ser Thr
        355                 360                 365
Val Asn Asn Leu Gln Glu Gln Leu Arg Lys Gln Val Ala Glu Ser Gln
370                 375                 380
Ala Lys Phe Ser Glu Phe Glu Arg Ser Asn Ser Asp Leu Val Ser Lys
385                 390                 395                 400
Leu Gln Thr Val Met Ser Arg Arg
                405

<210> SEQ ID NO 4
<211> LENGTH: 1227
<212> TYPE: DNA
<213> ORGANISM: Autographa californica nucleopolyhedrovirus

<400> SEQUENCE: 4
atgagtcgcc aaatcaacgc cgccactccc agcagcagcc gccgccacag gctgtctctc      60
agccgtcgcc gcatcaactt tacaacatct cccgaagccc agccgtcttc aagcagtcgc     120
agccagccgt cttcaagcag tcgcagccat cgccgtcagg agcggcgtca ggagcagcgt     180
gtcagcgaag aaaacgtgca gattatcggg aacgtcaacg agccgttgac gcgcacctac     240
catcgtcagg gtgtcacgta ttacgtgcac ggtcaggtta acattagcaa tgacgatccg     300
ctattaagtc aagaggatga cgtcatacta attaatagtg aaaatgtgga tcgtgaacgg     360
```

| | |
|---|---|
| tttcccgaca tcactgccca gcagtaccag gataacattg cgtcggagac agctgcgcag | 420 |
| agggctctgc aacgaggttt agatcttgag gctcagctga tgaatgagat tgccccaagg | 480 |
| tctcccactt atagtccatc ttattcgccg aattacgtaa taccacagtc gccagatttg | 540 |
| tttgcctcgc cgcagtctcc gcagccgcag cagcagcagc agcagcaatc agaacccgaa | 600 |
| gaagaagtag aggtttcgtg taatatttgt tttactactt ttaaagacac taaaaacgta | 660 |
| aattcctcgt ttgtgacttc gattcattgt aaccatgctg tgtgtttcaa gtgttatgtc | 720 |
| aagataatta tggacaattc tgtgtacaaa tgttttgca gcgctacttc atcagattgt | 780 |
| cgcgtgtaca ataagcacgg gtatgtgaaa tttatgccca ttaacgtcac tcgtaaccag | 840 |
| gattccatca acagcattg gcgcgagctt ttagaaaata acacggtcaa caatcacacc | 900 |
| acggacttga actatgtgga gcaattgcaa aaagaactgt ccgagctgcg agccaagacc | 960 |
| agccaagttg aacataaaat gaccatgtta aacagcgact acattatgct taaacacaag | 1020 |
| catgctgtcg ccgaattaga tttacaaaag gcaaactatg acttgcaaga atctaccaag | 1080 |
| aaatcagaag agttgcaatc gactgtgaat aatctgcaag aacaattgcg taagcaggtg | 1140 |
| gccgagtctc aagccaaatt ttcagagttt gagcgcagta actctgattt agtttctaag | 1200 |
| ttacaaactg ttatgtctag acgttaa | 1227 |

<210> SEQ ID NO 5
<211> LENGTH: 577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| attaatagta atcaattacg gggtcattag ttcatagccc atatatggag ttccgcgtta | 60 |
| cataacttac ggtaaatggc ccgcctggct gaccgcccaa cgacccccgc ccattgacgt | 120 |
| caataatgac gtatgttccc atagtaacgc caatagggac tttccattga cgtcaatggg | 180 |
| tggagtattt acggtaaact gcccacttgg cagtacatca agtgtatcat atgccaagtc | 240 |
| cgccccctat tgacgtcaat gacggtaaat ggcccgcctg gcattatgcc cagtacatga | 300 |
| ccttacggga ctttcctact tggcagtaca tctacgtatt agtcatcgct attaccatgc | 360 |
| tgatgcggtt ttggcagtac accaatgggc gtggatagcg gtttgactca cggggatttc | 420 |
| caagtctcca ccccattgac gtcaatggga gtttgttttg gcaccaaaat caacgggact | 480 |
| ttccaaaatg tcgtaataac cccgccccgt tgacgcaaat gggcggtagg cgtgtacggt | 540 |
| gggaggtcta tataagcaga gtcgtttag tgaaccg | 577 |

<210> SEQ ID NO 6
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | |
|---|---|
| aggcgtgtac ggtgggaggc ctatataagc agagctcgtt tagtgaaccg tcagatcgcc | 60 |
| tggagacgcc atccacgctg ttttgacctc catagaagac accgggaccg atccagcctc | 120 |
| cgcggccccg aattcgagct cgcagctggc | 150 |

<210> SEQ ID NO 7

```
<211> LENGTH: 326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ccaggcaggc agaagtatgc aaagcatgca tctcaattag tcagcaacca ggtgtggaaa      60
gtccccaggc tccccagcag gcagaagtat gcaaagcatg catctcaatt agtcagcaac     120
catagtcccg cccctaactc cgcccatccc gcccctaact ccgcccagtt ccgcccattc     180
tccgccccat ggctgactaa ttttttttat ttatgcagag gccgaggccg cctctgcctc     240
tgagctattc cagaagtagt gaggaggctt ttttggaggc ctaggctttt gcaaaaagct     300
cccgggagct tgtatatcca ttttcg                                          326

<210> SEQ ID NO 8
<211> LENGTH: 553
<212> TYPE: DNA
<213> ORGANISM: Autographa californica nucleopolyhedrovirus

<400> SEQUENCE: 8
catactcgag actagtaaat gacattatcc ctcgattgtg ttttacaagt agaattctac      60
ccgtaaagcg agtttagttt tgaaaaacaa atgacatcat tgtataatg acatcatccc     120 ctgattgtgt tttacaagta gaattctatc cgtaaagcga gttcagtttt gaaaacaaat     180
gagtcatacc taaacacgtt aataatcttc tgatatcagc ttatgactca agttatgagc     240
cgtgtgcaaa acatgagata agtttatgac atcatccact gatcgtgcgt tacaagtaga     300
attctactcg taaagccagt tcggttatga gccgtgtgca aaacatgaca tcagcttatg     360
actcatactt gattgtgttt tacgcgtaga attctactcg taaagcgagt tcggttatga     420
gccgtgtgca aaacatgaca tcagcttatg agtcataatt aatcgtgcgt tacaagtaga     480
attctactcg taaagcgagt tgaaggatca tatttagttg cgtttatgag ataagatgta     540
gtgctcgagt aaa                                                        553

<210> SEQ ID NO 9
<211> LENGTH: 118
<212> TYPE: DNA
<213> ORGANISM: Autographa californica nucleopolyhedrovirus

<400> SEQUENCE: 9
gttttacgag tagaattcta cgtgtaacac acgatctaaa agatgatgtc attttttatc      60
aatgactcat tgttttaaa acagacttgt tttacgagta gaattctacg tgtaaagc        118

<210> SEQ ID NO 10
<211> LENGTH: 669
<212> TYPE: DNA
<213> ORGANISM: Autographa californica nucleopolyhedrovirus

<400> SEQUENCE: 10
gctttacgag tagaattcta cgtgtaaaac ataatcaaga gatgatgtca tttgtttttc      60
aaaactgaac tcaagaaatg atgtcatttg ttttcaaaa ctgaactggc tttacgagta     120
gaattctact tgtaacgcat gatcaaggga tgatgtcatt tgttttcaa accgaactc     180 gctttacgag tagaattcta cttgtaaaac ataatcgaaa gatgatgtca tttgtttttt     240
aaaattgaac tggctttacg agtagaattc tacttgtaaa acacaatcga gagatgatgt     300
catattttgc acacggctct aattaaactc gctttacgag taaaattcta cttgtaacgc     360
```

```
atgatcaagg gatgatgtat tggatgagtc atttgttttt caaaactaaa ctcgctttac    420
gagtagaatt ctacttgtaa cgcacgccca agggatgatg tcatttattt gtgcaaagct    480
gatgtcatct tttgcacacg attataaaca caatcaaata atgactcatt tgttttcaa     540 aactgaactc gctttacgag tagaattcta cttgtaaaac acaatcaagc gatgatgtca    600
ttttaaaaat gatgtcattt gttttcaaa actaaactcg ctttacgagt agaattctac    660
gtgtaaaac                                                            669

<210> SEQ ID NO 11
<211> LENGTH: 30
<212> TYPE: DNA
<213> ORGANISM: Autographa californica nucleopolyhedrovirus

<400> SEQUENCE: 11
tttttacaaa tggaaatgta tttgtaaaac                                      30

<210> SEQ ID NO 12
<211> LENGTH: 666
<212> TYPE: DNA
<213> ORGANISM: Autographa californica nucleopolyhedrovirus

<400> SEQUENCE: 12
gatttacgcg tagaattcta cttgtaaagc aagttaaaat aagccgtgtg caaaaatgac     60
atcagacaaa tgacatcatc tacctatcat gatcatgtta ataatcatgt tttaaaatga   120
catcagctta tgactaataa ttgatcgtgc gttacaagta gaattctact cgtaaagcga   180
gtttagtttt gaaaaacaaa tgagtcatca ttaaacatgt taataatcgt gtataaagga   240
tgacatcatc cactaatcgt gcgttacaag tagaattcta ctcgtaaagc gagttcggtt   300
ttgaaaaaca aatgacatca tttcttgatt gtgttttaca cgtagaattc tactcgtaaa   360
gtatgttcag tttaaaaaac aaatgacatc attttacaga tgacatcatt tcttgattat   420
gttttacaag tagaattcta ctcgtaaagc aagtttagtt ttaaaaaaca aatgacatca   480
tctcttgatt atgttttaca gtagaattc tactcgtaaa gcgagtttag ttttgaaaaa    540
caaatgacat catctcttga ttatgtttta caagtagaat tctactcgta aagcgagttt   600
agttttcaaa aacaaatgac atcatcccctt gatcatgcgt acaagtaga attctactcg   660 taaagc                                                              666

<210> SEQ ID NO 13
<211> LENGTH: 150
<212> TYPE: DNA
<213> ORGANISM: Autographa californica nucleopolyhedrovirus

<400> SEQUENCE: 13
gcgttacaag tagaattcta ctggtaaagc aagttcggtt gtgagccgtg tgcaaaacat     60
gacatcataa ctaatcatgt ttataatcat gtgcaaaata tgacatcatc cgacgattgt   120
gttttacaag tagaattcta ctcgtaaagc                                    150

<210> SEQ ID NO 14
<211> LENGTH: 486
<212> TYPE: DNA
<213> ORGANISM: Autographa californica nucleopolyhedrovirus

<400> SEQUENCE: 14
gctttacgag tagaattta cttgtaaaac acaatcaaga aatgatgtca ttttgtacg       60 tgattataaa catgtttaaa catggtacat tgaacttaat ttttgcaagt tgataaacat   120
```

```
gattaatgta cgactcattt gtttgtgcaa gttgataaac gtgattaata tatgactcat    180
atgtttgtgc aaaaatgatg tcatcgtaca aactcgcttt acgagtagaa ttctacttgt    240
aacgcatgat caagggatga tgtcatttgt tttttttaaaa ttcaactcgc tttacgagta    300
gaattctact tgtaaaacac aatcgaggga tgatgtcatt tgtagaatga tgtcatttgt    360
ttttcaaaac cgaactcgct ttacgagtag aattctactt gtaacgcaag atcggtggat    420
gatgtcattt taaaaatgat gtcatcgtac aaactcgctt tacgagtaga attctacgtg    480
taaaac                                                               486

<210> SEQ ID NO 15
<211> LENGTH: 30
<212> TYPE: DNA
<213> ORGANISM: Autographa californica nucleopolyhedrovirus

<400> SEQUENCE: 15
gttttacgcg taaaattcta ctggtaaaac                                      30

<210> SEQ ID NO 16
<211> LENGTH: 509
<212> TYPE: DNA
<213> ORGANISM: Autographa californica nucleopolyhedrovirus

<400> SEQUENCE: 16
gctttacgag tagaattcta cgcgtaaaac acaatcaagt atgagtcata atctgatgtc     60
atgttttgta cacggctcat aaccgaactg gctttacgag tagaattcta cttgtaatgc    120
acgatcagtg gatgatgtca tttgttttc aaatcgagat gatgtcatgt tttgcacacg    180
gctcataaac tcgctttacg agtagaattc tacgtgtaac gcacgatcga ttgatgagtc    240
atttgttttg caatatgata tcatacaata tgactcattt gttttcaaa accgaacttg    300 atttacgggt agaattctac ttgtaaagca caatcaaaaa gatgatgtca tttgtttttc    360
aaaactgaac tcgctttacg agtagaattc tacgtgtaaa acacaatcaa gaaatgatgt    420
catttgttat aaaaataaaa gctgatgtca tgttttgcac atggctcata actaaactcg    480
ctttacgggt agaattctac gcgtaaaac                                      509

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catggccatg gtgacgcaaa ttaattttaa cgcgt                                35

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaccgctcga gattaaattc gaattttta ta                                    32

<210> SEQ ID NO 19
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccatgggt agtcgccaaa tcaacgcc                                         28

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcctcgagac gtctagacat aacagtttg                                        29

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccggctcgag taggcgtgta cggtgg                                           26

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctctcccc ggccgttggc cgattcatta atgc                                  34

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacattatc cctcgattgt gttttaca                                         28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgatccttca actcgcttta cgagtaga                                         28

<210> SEQ ID NO 25
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 25
tcaacgccga tccctatgat                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aacgtcgcca actcccattg                                                    20
```